(12) United States Patent
Policello et al.

(10) Patent No.: US 7,935,842 B2
(45) Date of Patent: May 3, 2011

(54) HYDROLYSIS RESISTANT ORGANOMODIFIED TRISILOXANE SURFACTANTS

(75) Inventors: George A. Policello, Ossining, NY (US); Mark D. Leatherman, Elmsford, NY (US); Wenqing Peng, Shanghai (CN); Suresh K. Rajaraman, Newburg, NY (US); Zijun Xia, Shanghai (CN)

(73) Assignee: Momentive Performance Materials Inc., Albany, NY (US)

( * ) Notice: Subject to any disclaimer, the term of this patent is extended or adjusted under 35 U.S.C. 154(b) by 1301 days.

(21) Appl. No.: 11/350,426

(22) Filed: Feb. 9, 2006

(65) Prior Publication Data

US 2007/0184005 A1  Aug. 9, 2007

(51) Int. Cl.
C07F 7/08 (2006.01)
(52) U.S. Cl. ......................... 556/456; 556/453
(58) Field of Classification Search ............... None
See application file for complete search history.

(56) References Cited

U.S. PATENT DOCUMENTS

| | | |
|---|---|---|
| 3,159,061 A | 12/1964 | Walker at al. |
| 3,220,972 A | 11/1965 | Lamoreaux |
| 3,299,112 A | 1/1967 | Bailey |
| 3,715,334 A | 2/1973 | Karstedt |
| 3,775,452 A | 11/1973 | Karstedt |
| 3,814,730 A | 6/1974 | Karstedt |
| 5,026,891 A | 6/1991 | Colas et al. |
| 5,104,647 A | 4/1992 | Policello |
| 5,401,871 A | 3/1995 | Feldmann-Krane et al. |
| 5,430,166 A | 7/1995 | Klein et al. |
| 5,430,167 A | 7/1995 | Klein et al. |
| 5,504,054 A * | 4/1996 | Murphy ............... 504/206 |
| 5,504,647 A | 4/1996 | Kuriyama |
| 5,558,806 A | 9/1996 | Policello et al. |
| 5,674,832 A | 10/1997 | Keys |
| 6,046,156 A | 4/2000 | Perry |
| 6,054,547 A | 4/2000 | Perry et al. |
| 6,060,546 A * | 5/2000 | Powell et al. ............ 524/267 |
| 6,075,111 A | 6/2000 | Perry et al. |
| 6,077,923 A | 6/2000 | Perry et al. |
| 6,083,901 A | 7/2000 | Perry et al. |
| 6,087,416 A | 7/2000 | Pearlstine et al. |
| 6,113,679 A | 9/2000 | Adkins et al. |
| 6,153,578 A | 11/2000 | Perry |
| 6,221,811 B1 | 4/2001 | Policello et al. |
| 6,255,511 B1 | 7/2001 | Klein et al. |
| 6,271,295 B1 | 8/2001 | Powell et al. |
| 6,300,283 B1 | 10/2001 | Sakuta |
| 6,489,498 B2 | 12/2002 | Klein et al. |
| 6,713,131 B2 | 3/2004 | Blackwood et al. |
| 2003/0104944 A1 | 6/2003 | Humble et al. |
| 2006/0030497 A1 | 2/2006 | Sperling |
| 2007/0184005 A1 | 8/2007 | Policello et al. |
| 2007/0197394 A1 | 8/2007 | Policello et al. |
| 2008/0090963 A1 | 4/2008 | Rajaraman et al. |
| 2008/0107696 A1 | 5/2008 | Czech et al. |

FOREIGN PATENT DOCUMENTS

| | | |
|---|---|---|
| EP | 0710500 B1 | 11/1994 |
| EP | 1 053 678 A | 11/2000 |
| GB | 1520421 | 10/1979 |
| WO | WO 94/22311 A | 10/1994 |
| WO | WO 2005/013693 A | 2/2005 |
| WO | WO 2006/017503 A1 | 2/2006 |

OTHER PUBLICATIONS

R. Wagner et al., (1998), "Silicon-Modified Carbohydrate Surfactants VII: Impact of Different Silicon Substructures on the Wetting Behaviour of Carbohydrate Surfactants on Low-Energy Surfaces—Distance Decay of Donor-Acceptor Forces", Applied Organometallic Chemistry 12, 265-276.
R. Wagner et al., (1997), "Silicon-Modified Carbohydrate Surfactants V: The Wetting Behaviour of Low-Molecular-Weight Siloxane, Carbosilane, Silane and Polysilane Precursors on Low-Energy Surfaces", Applied Organometallic Chemistry 11, 645-657.
Perry, D; Zeng, J.; O'Neill, V.; Foam Control in Aqueous Coatings, p. 1-4, Dow Corning, 2004 [online], accessed via the internet [retrieved on Aug. 19, 2009], URL: >http://www.dowcoming.com/content/publishedlit/26-1231-01_Foam_control_Aq_Coatings_WP.pdf>.
MSDS for Dow Coming Antifoam 1400 [online], accessed via the internet [retrieved on Aug. 19, 2009], URL:<http://www2.dowcoming.com/DataFiles/090007b28113c0dc.pdf>.
Davison, G.; Lane, B.; Additives in Water-borne Coatings, p. 77-81, Royal Society of Chemistry, 2003.

* cited by examiner

*Primary Examiner* — Daniel M Sullivan
*Assistant Examiner* — Yevegeny Valenrod
(74) *Attorney, Agent, or Firm* — Dominick G. Vicari (57) ABSTRACT

Three types of trisiloxane surfactants having the basic formula:

MDM' are described wherein the substituents on the differing M and M' groups in conjunction with a pendant polyalkylene oxide substituents on the D group to render the surfactant resistant to hydrolysis under either basic or acidic conditions.

70 Claims, No Drawings

HYDROLYSIS RESISTANT ORGANOMODIFIED TRISILOXANE SURFACTANTS

FIELD OF THE INVENTION

The present invention relates to trisiloxane surfactant compositions that exhibit resistance to hydrolysis over a wide pH range. More particularly the present invention relates to such hydrolysis resistant trisiloxane surfactants having a resistance to hydrolysis between a pH of about 3 to a pH of about 12.

BACKGROUND OF THE INVENTION

The topical application of liquid compositions to the surfaces of both animate and inanimate objects to effect a desired change involve the processes of controlling wetting, spreading, foaming, detergency, and the like. When used in aqueous solutions to improve the delivery of active ingredients to the surface being treated, trisiloxane type compounds have been found to be useful in enabling the control of these processes to achieve the desired effect. However, the trisiloxane compounds may only be used in a narrow pH range, ranging from a slightly acidic pH of 6 to a very mildly basic pH of 7.5. Outside this narrow pH range, the trisiloxane compounds are not stable to hydrolysis undergoing a rapid decomposition.

SUMMARY OF THE INVENTION

The present invention provides for a trisiloxane compound or compositions thereof useful as a surfactant selected from the group of trisiloxane compounds having the formula I, II or III.

Trisiloxane compound I has the formula:

$$M^1 D^1 M^2$$

wherein $$M^1 = (R^1)(R^2)(R^3)SiO_{1/2}$$

$$M^2 = (R^4)(R^5)(R^6)SiO_{1/2}$$

$$D^1 = (R^7)(Z)SiO_{2/2}$$

where
$R^1$ is selected from a branched or linear hydrocarbon group consisting of 2 to 4 carbons, aryl, and an alkyl hydrocarbon group of 4 to 9 carbons containing aryl substituents of 6 to 20 carbon atoms; $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group; Z is an alkyleneoxide group of the general formula:
$R^8(C_2H_4O)_a(C_3H_6O)_b(C_4H_8O)_cR^9$, where $R^8$ is a linear or branched divalent hydrocarbon radical of 2, 3, 5, 6, 7, 8, or 9 carbon atoms; $R^9$ is selected from the group consisting of H, monovalent hydrocarbon radicals of from 1 to 6 carbon atoms and acetyl the subscripts a, b and c are zero or positive and satisfy the following relationships:

$$2 \leq a+b+c \leq 20 \text{ with } a \geq 2.$$

When the subscript a satisfies the condition $2 \leq a \leq 5$ it is advisable to utilize a co-surfactant as hereinafter set forth in order to obtain the benefit of the compositions of the present invention.

Trisiloxane compound II has the formula:

$$M^3 D^2 M^4$$

wherein $$M^3 = (R^{10})(R^{11})(R^{12})SiO_{1/2}$$

$$M^4 = (R^{13})(R^{14})(R^{15})SiO_{1/2}$$

$$D^2 = (R^{16})(Z')SiO_{2/2}$$

where $R^{10}$, $R^{11}$, $R^{12}$ $R^{13}$, $R^{14}$, $R^{15}$ and $R^{16}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms; Z' is an alkylene oxide group of the general formula:
$R^{17}(C_2H_4O)_d(C_3H_6O)_e(C_4H_8O)_f R^{18}$, where $R^{17}$ is selected from a branched or linear divalent hydrocarbon radical of the general formula:

$$-C_4H_8O-(C_2H_4O)-$$

$R^{18}$ is selected from the group consisting of H, monovalent hydrocarbon radicals of from 1 to 6 carbon atoms and acetyl the subscripts d, e and f are zero or positive and satisfy the following relationships:

$$2 \leq d+e+f \leq 20 \text{ with } d \geq 2.$$

When the subscript d satisfies the condition $2 \leq d \leq 5$ it is advisable to utilize a co-surfactant as hereinafter set forth in order to obtain the benefit of the compositions of the present invention.

Trisiloxane compound III has the formula:

$$M^5 D^3 M^6$$

wherein $$M^5 = (R^{19})(R^{20})(R^{21})SiO_{1/2}$$

$$M^6 = (R^{22})(R^{23})(R^{24})SiO_{1/2}$$

$$D^3 = (R^{25})(Z'')SiO_{2/2}$$

where
$R^{19}$, $R^{20}$, $R^{21}$, $R^{22}$, $R^{23}$, and $R^{24}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms, $R^{25}$ is a linear or branched hydrocarbon radical of 2 to 4 carbons; Z" is an alkylene oxide group of the general formula:
$R^{26}(C_2H_4O)_g(C_3H_6O)_h(CH_8O)_i R^{27}$, where $R^{26}$ is a linear or branched divalent hydrocarbon radical of 2, 3, 5, 6, 7, 8, or 9 carbon atoms; $R^{27}$ is selected from the group consisting of H, monovalent hydrocarbon radicals of from 1 to 6 carbon atoms and acetyl the subscripts g, h and i are zero or positive and satisfy the following relationships:

$$2 \leq g+h+i \leq 20 \text{ with } g \geq 2.$$

When the subscript g satisfies the condition $2 \leq g \leq 5$ it is advisable to utilize a co-surfactant as hereinafter set forth in order to obtain the benefit of the compositions of the present invention.

DETAILED DESCRIPTION OF THE INVENTION

As used herein, integer values of stoichiometric subscripts refer to molecular species and non-integer values of stoichiometric subscripts refer to a mixture of molecular species on a molecular eight average basis, a number average basis or a mole fraction basis.

The present invention provides for a trisiloxane compound or compositions thereof useful as a surfactant selected from the group of trisiloxane compounds having the formula I, II or III.

Trisiloxane compound I has the formula:

$$M^1D^1M^2$$

wherein $$M^1=(R^1)(R^2)(R^3)SiO_{1/2}$$

$$M^2=(R^4)(R^5)(R^6)SiO_{1/2}$$

$$D^1=(R^7)(Z)SiO_{2/2}$$

where
$R^1$ is selected from a branched or linear hydrocarbon group consisting of 2 to 4 carbons, aryl, and an alkyl hydrocarbon group of 4 to 9 carbons containing an aryl substituents of 6 to 20 carbon atoms; $R^2, R^3, R^4, R^5, R^6$ and $R^7$ are each independently selected from the group consisting of 1 to 4 carbon monovalent hydrocarbon radicals, aryl, and a hydrocarbon group of 4 to 9 carbons containing an aryl group. Z is an alkyleneoxide group of the general formula:
$R^8(C_2H_4O)_a(C_3H_6O)_b(C_4H_8O)_cR^9$, where $R^8$ is a linear or branched divalent hydrocarbon radical of 2, 3, 5, 6, 7, 8, or 9 carbon atoms; $R^9$ is selected from the group consisting of H, monovalent hydrocarbon radicals of from 1 to 6 carbon atoms and acetyl the subscripts a, b and c are zero or positive and satisfy the following relationships:

$$2 \leq a+b+c \leq 20 \text{ with } a \geq 2.$$

When the subscript a satisfies the condition $2 \leq a \leq 5$ it is advisable to utilize a co-surfactant as hereinafter set forth in order to obtain the benefit of the compositions of the present invention.

Trisiloxane compound II has the formula:

$$M^3D^2M^4$$

wherein $$M^3=(R^{10})(R^{11})(R^{12})SiO_{1/2}$$

$$M^4=(R^{13})(R^{14})(R^{15})SiO_{1/2}$$

$$D^2=(R^{16})(Z')SiO_{2/2}$$

where $R^{10}, R^{11}, R^{12}, R^{13}, R^{14}, R^{15}$ and $R^{16}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms; Z' is an alkylene oxide group of the general formula:
$R^{17}(C_2H_4O)_d(C_3H_6O)_e(C_4H_8O)_fR^{18}$, where $R^{17}$ has the formula:

$$C_4H_8O-(C_2H_4O)-$$

$R^{18}$ is selected from the group consisting of H, monovalent hydrocarbon radicals of from 1 to 6 carbon atoms and acetyl the subscripts d, e and f are zero or positive and satisfy the following relationships:

$$2 \leq d+e+f \leq 20 \text{ with } d \geq 2.$$

When the subscript d satisfies the condition $2 \leq d \leq 5$ it is advisable to utilize a co-surfactant as hereinafter set forth in order to obtain the benefit of the compositions of the present invention.

Trisiloxane compound III has the formula:

$$M^5D^3M^6$$

wherein $$M^5=(R^{19})(R^{20})(R^{21})SiO_{1/2}$$

$$M^6=(R^{22})(R^{23})(R^{24})SiO_{1/2}$$

$$D^3=(R^{25})(Z'')SiO_{2/2}$$

where
$R^{19}, R^{20}, R^{21}, R^{22}, R^{23}$, and $R^{24}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms, $R^{25}$ is a linear or branched hydrocarbon radical of 2 to 4 carbons; Z'' is an alkylene oxide group of the general formula:
$R^{26}(C_2H_4O)_g(C_3H_6O)_h(C_4H_8O)_iR^{27}$, where $R^{26}$ is a linear or branched divalent hydrocarbon radical of 2, 3, 5, 6, 7, 8, or 9 carbon atoms;

$R^{27}$ is selected from the group consisting of H, monovalent hydrocarbon radicals of from 1 to 6 carbon atoms and acetyl the subscripts g, h and i are zero or positive and satisfy the following relationships:

$$2 \leq g+h+i \leq 20 \text{ with } g \geq 2.$$

When the subscript g satisfies the condition $2 \leq g \leq 5$ it is advisable to utilize a co-surfactant as hereinafter set forth in order to obtain the benefit of the compositions of the present invention.

One method of producing the composition of the present invention is to react a molecule of the following formula:

$$MD^HM$$

where $D^H$ is the hydride precursor to the D' structural unit in the composition of the present invention, wherein the definitions and relationships are later defined and consistent with those defined above, under hydrosilylation conditions, with an olefinically modified polyalkyleneoxide, such as allyloxy-polyethyleneglycol, or methallyloxypolyalkyleneoxide, which are incorporated here as examples, and not set forth to limit other possible olefinically modified alkyleneoxide components. As use herein the phrase "olefinically modified polyalkyleneoxide" is defined as a molecule possessing one or more alkyleneoxide groups containing one or more, terminal or pendant, carbon-carbon double bonds. The polyether (the precursor to the substituents Z, Z' or Z'') is an olefinically modified polyalkyleneoxide (hereinafter referred to as "polyether") is described by the general formula:

$$CH_2=CH(R^{28})(R^{29})_jO(R^{30})_k(C_2H_4O)_m(C_3H_6O)_n(C_4H_8O)_pR^{31}$$

where
$R^{28}$ is H or methyl; $R^{29}$ is a divalent alkyl radical of 1 to 6 carbons where the subscript j may be 0 or 1; $R^{30}$ is $-C_2H_4O-$, where the subscript k may be 0 or 1; $R^{31}$ is H, a monofunctional hydrocarbon radical of 1 to 6 carbons, or acetyl and the subscripts m, n and p are zero or positive and satisfy the relationship $2 \leq m+n+p \leq 20$ with $m \geq 2$. When the polyether is composed of mixed oxyalkyleneoxide groups (i.e. oxyethylene, oxypropylene and oxybutylene) the units may be blocked, or randomly distributed. One skilled in the art will understand the advantages of using a blocked or random configuration. Illustrative examples of blocked configurations are: -(oxyethylene)$_a$(oxypropylene)$_b$-; -(oxybutylene)$_c$(oxyethylene)$_a$-; and -(oxypropylene)$_b$(oxyethylene)$_a$(oxybutylene)$_c$-.

Illustrative examples of the polyether are provided below, but not limited to:

$CH_2=CHCH_2O(CH_2CH_2O)_8H$; $CH_2=CHCH_2O(CH_2CH_2O)_8CH_3$; $CH_2=CHCH_2O(CH_2CH_2O)_4(CH_2CH(CH_3)O)_5H$; $CH_2=CHO(CH_2CH_2O)_5(CH_2CH(CH_3)O)_5H$; $CH_2=C(CH_3)CH_2O(CH_2CH_2O)_4$ $(CH_2CH(CH_3)O)_5C(=O)CH_3$; $CH_2=CHCH_2O(CH_2CH_2O)_5(CH_2CH(CH_3)O)_2(CH_2CH(CH_2CH_3)O)_2H$

Polyether modified siloxanes are prepared in the normal manner through the use of a hydrosilylation reaction to graft the olefinically modified (i.e. vinyl, allyl or methallyl) polyalkyleneoxide onto the hydride (SiH) intermediate of the trisiloxane of the present invention.

A preferred embodiment of trisiloxane compound formula I is where $R^1$ and $R^4$ are selected from a branched or linear hydrocarbon group consisting of 2 to 4 carbons, aryl, an alkyl hydrocarbon group of 4 to 9 carbons containing an aryl substituents of 6 to 20 carbon atoms; More preferably 3 to 4 carbons or aryl. $R^2$, $R^3$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group; more preferably 1 to 2 carbon monohydrocarbon radicals and aryl; most preferably methyl. Z is an alkyleneoxide group of the general formula:

$R^8(C_2H_4O)_a(C_3H_6O)_b(C_4H_8O)_cR^9$, where $R^8$ is a linear or branched divalent hydrocarbon radical of 2, 3, 5, 6, 7, 8, or 9 carbon atoms, more preferably 3 to 7 carbons; most preferably 3 to 6 carbons. Subscripts a, b and c are zero or positive and satisfy the following relationships:

$2 \leq a+b+c \leq 20$ with $a \geq 2$; preferably a is 5 to 20, more preferably 5 to 8; preferably b is 0 to 10; more preferably 0 to 5; preferably c is 0 to 8, more preferably 0 to 4. $R^9$ is selected from the group consisting of H, monovalent hydrocarbon radicals of from 1 to 6 carbon atoms and acetyl.

Another preferred embodiment of trisiloxane compound formula I is where $R^1$, $R^4$ and $R^7$ are selected from a branched or linear hydrocarbon group consisting of 2 to 4 carbons, and aryl; more preferably 3 to 4 carbons. $R^2$, $R^3$, $R^5$ and $R^6$ are each independently selected from the group consisting of 1 to 4 carbon monovalent hydrocarbon radicals, and aryl; more preferably 1 to 2 carbons; most preferably methyl. Z is as described above.

A preferred embodiment of trisiloxane compound formula II is where $R^{10}$, $R^{11}$, $R^{12}R^{13}$, $R^{14}$, $R^{15}$ and $R^{16}$ are each independently selected from the group consisting of 1 to 4 carbon monovalent hydrocarbon radicals, and aryl; Z' is an alkylene oxide group of the general formula:

$R^{17}(C_2H_4O)_d(C_3H_6O)_e(C_8H_8O)_fR^{18}$, where $R^{17}$ is selected from a branched or linear divalent hydrocarbon radical of the general formula:

—$C_4H_8O$—$(C_2H_4O)$—

$R^{18}$ is selected from the group consisting of H, monovalent hydrocarbon radicals of from 1 to 6 carbon atoms and acetyl; more preferably H, and monovalent hydrocarbon radicals of from 1 to 4 carbon atoms; the subscripts d, e and f are zero or positive and satisfy the following relationships:

$2 \leq d+e+f \leq 20$ with $d \geq 2$; preferably d is 5 to 20, more preferably 5 to 8; preferably e is 0 to 10; more preferably 0 to 5; preferably f is 0 to 8, more preferably 0 to 4.

A preferred embodiment of trisiloxane compound formula III is where:

$R^{19}$, $R^{20}$, $R^{21}$, $R^{22}$, $R^{23}$, and $R^{24}$ are each independently selected from the group consisting of 1 to 4 carbon monovalent hydrocarbon radicals and aryl; $R^{25}$ is a linear or branched hydrocarbon radical of 2 to 4 carbons; most preferred 3 to 4 carbons; Z" is an alkylene oxide group of the general formula:

$R^{26}(C_2H_4O)_g(C_3H_6O)_h(C_4H_8O)_iR^{27}$, where $R^{26}$ is a linear or branched divalent hydrocarbon radical of 2, 3, 5, 6, 7, 8, or 9 carbon atoms; more preferably 3 to 7 carbons; most preferably 3 to 6 carbons.

$R^{27}$ is selected from the group consisting of H, monovalent hydrocarbon radicals of from 1 to 6 carbon atoms and acetyl; more preferably H, and monovalent hydrocarbon radicals of from 1 to 4 carbon atoms; the subscripts g, h and i are zero or positive and satisfy the following relationships:

$2 \leq g+h+i \leq 20$ with $g \geq 2$; preferably g is 5 to 20, more preferably 5 to 8; preferably h is 0 to 10; more preferably 0 to 5; preferably i is 0 to 8, more preferably 0 to 4.

Precious metal catalysts suitable for making polyether substituted siloxanes are also well known in the art and comprise complexes of rhodium, ruthenium, palladium, osmium, iridium, and/or platinum. Many types of platinum catalysts for this SiH olefin addition reaction are known and such platinum catalysts may be used to generate the compositions of the present invention. The platinum compound can be selected from those having the formula ($PtCl_2Olefin$) and $H(PtCl_3Olefin)$ as described in U.S. Pat. No. 3,159,601, hereby incorporated by reference. A further platinum containing material can be a complex of chloroplatinic acid with up to 2 moles per gram of platinum of a member selected from the class consisting of alcohols, ethers, aldehydes and mixtures thereof as described in U.S. Pat. No. 3,220,972 hereby incorporated by reference. Yet another group of platinum containing materials useful in this present invention is described in U.S. Pat. Nos. 3,715,334; 3,775,452 and 3,814,730 (Karstedt). Additional background concerning the art may be found in J. L. Spier, "Homogeneous Catalysis of Hydrosilation by Transition Metals", in Advances in Organometallic Chemistry, volume 17, pages 407 through 447, F. G. A. Stone and R. West editors, published by Academic Press (New York, 1979). Those skilled in the art can easily determine an effective amount of platinum catalyst. Generally an effective amount ranges from about 0.1 to 50 parts per million of the total organomodified trisiloxane composition.

The compositions of the present invention exhibit an enhanced resistance to hydrolysis outside a pH range ranging from 6 to 7.5. Enhanced resistance to hydrolysis can be demonstrated by a variety of tests but as used herein enhanced resistance to hydrolysis means 50 mole percent or more of the hydrolysis resistant composition of the present invention remains unchanged or unreacted after a period of a twenty-four exposure to aqueous acidic conditions where the solution has a pH lower than 6 or after a period of a twenty-four hour exposure to aqueous basic conditions where the solution has a pH greater than 7.5. Under acidic conditions the compositions of the present invention show a survival of 50 mole percent of the original concentration or greater at a pH of 5 or less for a period of time in excess of 48 hours; specifically the compositions of the present invention show a survival of 50 mole percent or greater at a pH of 5 or less for a period of time in excess of 2 weeks; more specifically the compositions of the present invention show a survival of 50 mole percent or greater at a pH of 5 or less for a period of time in excess of 1 month; and most specifically the compositions of the present invention show a survival of 50 mole percent or greater at a pH of 5 or less for a period of time in excess of 6 months. Under basic conditions the compositions of the present invention show a survival of 50 mole percent or greater at a pH of 8 or more for a period of time in excess of 2 weeks; specifically the compositions of the present invention show a survival of 50 mole percent or greater at a pH of 8 or more for a period of time in excess of 4 weeks; more specifically the compositions of the present invention show a survival of 50 mole percent or greater at a pH of 8 or more for a period of time in excess of 6 months; and most specifically the compositions of the present invention show a survival of 50 mole percent or greater at a pH of 8 or more for a period of time in excess of 1 year.

Uses for the Compositions of the Present Invention:

A. Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the organomodified trisiloxane surfactant of the present invention is present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, Bacillus thuringiensis, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the organomodified trisiloxanes of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1-3-pentane diol and alkoxylated (especially ethoxylated) versions thereof as illustrated in U.S. Pat. No. 5,674,832 herein incorporated by reference, or n-methyl-pyrrilidone.

Co-Surfactants:

Moreover, other co-surfactants, which have short chain hydrophobes that do not interfere with superspreading as described in U.S. Pat. Nos. 5,558,806; 5,104,647; and 6,221,811 are herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFO-NYL-Air Products), pyrrilodone based surfactants (e.g., SURFADONE-LP 100-ISP), 2-ethyl hexyl sulfate, isodecyl alcohol ethoxylates (e.g., RHODASURF DA 530-Rhodia), ethylene diamine alkoxylates (TETRONICS-BASF), and ethylene oxide/propylene oxide copolymers (PLURONICS-BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates; and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Ouest (Helena Chemical, Collierville, Tenn.), modified clays such as Surround® (Englehard Corp.), foam control agents, surfactants, wetting agents, dispersants, emulsifiers, deposition aids, anti-drift components, and water.

Suitable agrochemical compositions are made by combining, in a manner known in the art, such as, by mixing one or more of the above components with the organomodified trisiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

B. Coatings:

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as, Solvent-borne coatings, water-borne coatings and powder coatings.

The coatings components may be employed as: Architecture coatings; OEM product coatings such as Automotive coatings and coil coatings; Special Purpose coatings such as industrial maintenance coatings and marine coatings;

Typical resin types include: Polyesters, alkyds, acrylics, epoxies

C. Personal Care

In a preferred embodiment, the organomodified trisiloxane surfactant of the present invention comprises, per 100 parts by weight ("pbw") of the personal care composition, from 0.1 to 99 pbw, more preferably from 0.5 pbw to 30 pbw and still more preferably from 1 to 15 pbw of the organomodified trisiloxane surfactant and from 1 pbw to 99.9 pbw, more preferably from 70 pbw to 99.5 pbw, and still more preferably from 85 pbw to 99 pbw of the personal care composition.

The organomodified trisiloxane surfactant compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may be render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the organomodified trisiloxane surfactant of the present invention;

2) aqueous emulsions where the continuous phase comprises the organomodified trisiloxane surfactant of the present invention and the discontinuous phase comprises water;

3) non-aqueous emulsions where the discontinuous phase comprises a non-aqueous hydroxylic solvent and the continuous phase comprises the organomodified trisiloxane surfactant of the present invention; and 4) non-aqueous emulsions where the continuous phase comprises a non-aqueous hydroxylic organic solvent and the discontinuous phase comprises the organomodified trisiloxane surfactant of the present invention.

Non-aqueous emulsions comprising a silicone phase are described in U.S. Pat. No. 6,060,546 and U.S. Pat. No. 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the organomodified trisiloxane surfactant of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the organomodified trisiloxane surfactant. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the organomodified trisiloxane surfactant of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the organomodified trisiloxane surfactant, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the organomodified trisiloxane surfactant, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions, other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

EXPERIMENTAL

The hydride intermediates for the organomodified trisiloxane surfactant compositions of the present invention, as well as comparative compositions were prepared as described in the following examples.

Preparation Example 1

Figure 1:
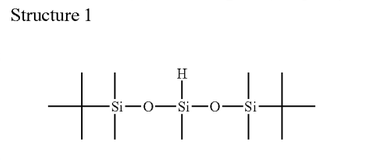

1,5-di(t-butyl)-1,1,3,5,5, Pentamethyltrisiloxane (Figure 1, Structure 1).

100 g tBuMe2SiCl and 46 g MeHSiCl$_2$ were dissolved in 150 ml isopropylether (IPE) and placed in an addition funnel. 150 g water and 250 ml IPE were charged into a 1 L round bottom flask equipped with a mechanical stirrer, reflux condenser and N$_2$ inlet. The chlorosilanes were added dropwise via the addition funnel at room temperature (23° C.) over a period of 1 h. After addition was completed, the temperature was adjusted to 70° C. and the reaction was run at reflux temperature for 20 h and progress followed by GC (88% yield at 20 h). When the reaction was finished, the water was drained off via a separation funnel. The fluid was washed 3 times using 100 g of water each time. 25 g of NaHCO$_3$ was mixed with 10 g of water and added slowly to the mixture and stirred for 30 min. The water was again drained and dried over sodium sulfate. After filtering, the IPE was stripped off on the rotor evaporator and the crude product was further fractional distilled under reduced pressure to afford 63 g tBuMe2SiOMe(H)SiOSi Me$_2$tBu (GC purity 97%).

Structure 1

Preparation Example 2

1,5-di(isopropyl)-1,1,3,5,5, Pentamethyltrisiloxane (Figure 2, Structure 2).

25 g iPrMe2SiCl (0.183 moles) and 13.1 g MeHSiCl$_2$ (0.114 moles) were dissolved in 80 ml isopropylether (IPE) and placed in an addition funnel. 50 g water and 100 ml IPE were charged into a 500 ml round bottom flask equipped with a mechanical stirrer, reflux condenser and N$_2$ inlet. The chlorosilanes were added dropwise via the addition funnel at room temperature (23° C.) over a period of 40 min. After addition was completed, the temperature was adjusted to 80° C. and the reaction was run at reflux temperature for 4 h and progress followed by GC (75% yield at 4 h). When the reaction was finished, the water was drained off via a separation funnel. The fluid was washed 3 times using 80 g of water each time. 25 g of NaHCO$_3$ was mixed with 100 g of water and added slowly to the mixture and stirred for 30 min. The water was again drained and dried over sodium sulfate. After filtering, the IPE was stripped off on the rotor evaporator and the crude product was further fractional distilled under reduced pressure to afford 10 g iPrMe$_2$SiOMe(H)SiOSi Me$_2$iPr (GC purity 93%).⟶

Structure 2

Preparation Example 3

The hydride intermediates of Examples 1-2 were further modified with various allylpolyalkyleneoxides to yield the organomodified trisiloxane surfactant compositions of the present invention (Table 1), as well as the comparative trisiloxane surfactants (From Table 2).

The organomodified trisiloxane surfactant compositions of the present invention were prepared by conventional methods of platinum mediated hydrosilation, as described in Bailey, U.S. Pat. No. 3,299,112, herein incorporated by reference.

Table 1 provides a description of the compositions of the present invention. Some of these compositions are described by the structure:

M*D'M* where M*=R$^1$Si(CH$_3$)$_2$O$_{0.5}$;
D'=OSi(CH$_3$)CH$_2$CH(R$^{32}$)CH$_2$O—(CH$_2$CH$_2$O)$_r$—(CH$_2$CH$_2$O)sR$^{33}$ where R$^1$, R$^{32}$, R$^{33}$, subscripts r, and s are described in Table 1.

TABLE 1

Description of Organomodified Trisiloxane Surfactant Compositions

| I.D. | R$^1$ | R$^{13}$ | r | s | R$^{33}$ |
|---|---|---|---|---|---|
| 1 | (CH$_3$)$_3$C— | H | 0 | 11 | H |
| 2 | (CH$_3$)$_2$CH$_2$— | H | 0 | 11 | H |
| 3 | CH$_3$— | CH$_3$ | 1 | 7.5 | CH$_3$ |

Table 2 provides a description of the comparative trisiloxane and organosilicone polyether based surfactants of the general structure:

MD$_x$D"$_y$M where

M=(CH$_3$)$_3$SiO$_{0.5}$; D=OSi(CH$_3$)$_2$; and

D"=OSi(CH$_3$)CH$_2$CH$_2$CH$_2$O—(CH$_2$CH$_2$O)$_d$R$^9$

TABLE 2

Composition of Comparative Organosilicone Polyether Surfactants

| | | | Polyether Group | |
| I.D. | X | Y | d | R$^9$ |
|---|---|---|---|---|
| A | 0 | 1 | 7.5 | CH$_3$ |
| B | 0 | 1 | 7.5 | H |
| C | 20 | 3 | 7.5 | CH$_3$ |

Additionally, comparative sample OPE (Octylphenolethoxylate, containing 10 polyoxyethylene units) is a non-silicone organic surfactant. This product is available as Triton® X-100 from Dow Chemical Company, Midland, Mich.

Example 4

This example demonstrates the ability of the organomodified trisiloxane composition of the present invention to reduce aqueous surface tension thereby showing utility as surfactants. Surface tension was measured using a Kruss surface tensiometer, with a sand blasted platinum blade as the sensor. Solutions of the various components were prepared at 0.1 wt % in 0.005M NaCl water (Deionized), as an equilibrium aid.

Table 3 shows that solutions of these unique compositions provide a significant reduction in surface tension relative to the conventional surfactant.

The compositions of the present invention also provide spreading properties similar to the comparative trisiloxane surfactants (A, B). Additionally, organomodified trisiloxane surfactants of the present invention provide improved spreading relative to the conventional silicone polyether (C) and conventional organic surfactant product OPE.

Spreading was determined by applying a 10 μL droplet, of surfactant solution to polyacetate film (USI, "Crystal Clear Write on Film") and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 3

Surface Tension and Spreading Properties

| | Surface Tension | Spread Diameter (mm) Weight % Surfactant | | | |
| I.D. | mN/m | 0.05% | 0.1% | 0.2% | 0.4% |
|---|---|---|---|---|---|
| 1 | 23.1 | 9 | 11 | 12 | 15 |
| 2 | 23.6 | 10 | 13 | 16 | 25 |
| 3 | 20.7 | 18 | 31 | 48 | 56 |
| A | 20.9 | 34 | 53 | 51 | 25 |
| B | 20.6 | 37 | 53 | 50 | 35 |
| C | 23.6 | nd | nd | nd | 6 |
| OPE | 31.8 | nd | 9 | nd | 10 |

Example 5

Hydrolytic stability was determined for representative compositions of the present invention using HPLC. Solutions of the various compositions were prepared at 0.5 wt % over a pH range from pH 4 to pH11, and monitored by HPLC for decomposition as a function of time.

Analytical Method:

The samples were analyzed by a reverse-phase chromatographic technique using the experimental conditions listed in Table 4.

TABLE 4

Solvent Gradient for HPLC Method

| Time (min.) | % Methanol | % Water | % Isopropanol |
|---|---|---|---|
| 0.0 | 70 | 30 | 0 |
| 15.0 | 100 | 0 | 0 |
| 20.0 | 50 | 0 | 50 |
| 20.1 | 70 | 30 | 0 |
| 25.0 | 70 | 30 | 0 |

Detector: ELSD/LTA (Evaporative Light Scattering with Low Temperature Adapter

Conditions: 30° C., 1.95 SLPM $N_2$

Column: Phenomenex LUNA C18 end cap, 5 micron, 75×4.6 mm

Flow Rate: 1.0 mL/min.

Inj. Volume: 10 microliters

Sample: 0.050 g/mL in methanol

Tables 5-8 demonstrates that the compositions of the present invention provide improved resistance to hydrolytic decomposition relative to the standard comparative siloxane based surfactant Siloxane A, under similar pH conditions.

Comparative siloxane A shows rapid hydrolysis at pH values below 5 and at pH values above 7, while the organomodified trisiloxane surfactants of the present invention demonstrates a higher resistance to hydrolysis under the same conditions.

TABLE 5

Hydrolytic Stability of Siloxane Based Surfactants by HPLC

| | | Stability: % Siloxane Surfactant Remaining | | | | | |
|---|---|---|---|---|---|---|---|
| I.D. | Time | pH 4 | pH 5 | pH 7 | pH 9 | pH 10 | pH 11 |
| 1 | 24 h | 100 | 100 | 100 | 100 | 100 | 100 |
| | 1 wk | 100 | 100 | 100 | 100 | 100 | 100 |
| | 2 wk | 100 | 100 | 100 | 100 | 100 | 100 |
| | 4 wk | 100 | 100 | 100 | 100 | 100 | 100 |
| | 6 wk | 100 | 100 | 100 | 100 | 100 | 100 |
| | 9 wk | 100 | 100 | 100 | 100 | 100 | 100 |
| | 12 wk | 100 | 100 | 100 | 100 | 100 | 100 |
| | 17 wk | 60 | 100 | 100 | 100 | 100 | 100 |
| | 23 wk | 45 | 100 | 100 | 100 | 100 | 100 |
| | 28 wk | 30 | 100 | 100 | 100 | 100 | 21 |

TABLE 6

Hydrolytic Stability of Siloxane Based Surfactants by HPLC

| | | Stability: % Siloxane Surfactant Remaining | | | | | |
|---|---|---|---|---|---|---|---|
| I.D. | Time | pH 4 | pH 5 | pH 7 | pH 9 | pH 10 | pH 11 |
| 2 | 24 h | 100 | 100 | 100 | 100 | 100 | 100 |
| | 10 days | 100 | 100 | 100 | 100 | 100 | 100 |
| | 5 wk | 100 | 100 | 100 | 100 | 100 | 100 |

TABLE 7

Hydrolytic Stability of Siloxane Based Surfactants by HPLC

| | | Stability: % Siloxane Surfactant Remaining | | | | | |
|---|---|---|---|---|---|---|---|
| I.D. | Time | pH 4 | pH 5 | pH 7 | pH 9 | pH 10 | pH 11 |
| 3 | 24 h | 100 | 100 | 100 | 100 | 100 | 100 |
| | 1 wk | 40 | 92 | 100 | 99 | 73 | 0 |
| | 2 wk | 24 | 82 | 100 | 94 | 48 | nd |
| | 3 wk | 16 | 75 | 100 | 92 | 43 | nd |
| | 5 wk | 6 | 65 | 100 | 89 | 35 | nd |
| | 7 wk | 2 | 55 | 100 | 82 | 29 | nd |
| | 24 wk | 0 | 21 | 100 | 50 | 4 | nd |
| | 31 wk | nd | 0.2 | 100 | 42 | 0.3 | nd |

TABLE 8

Hydrolytic Stability of Comparative Siloxane Based Surfactants by HPLC

| | | Stability: % Siloxane Surfactant Remaining | | | | | |
|---|---|---|---|---|---|---|---|
| I.D. | Time | pH 4 | pH 5 | pH 7 | pH 9 | pH 10 | pH 11 |
| A | 48 h | 25 | 100 | 100 | 100 | 46 | nd |
| | 1 wk | 0 | 38 | 100 | 53 | 0 | nd |

Example 6

Unlike traditional siloxane based surfactants, which are subject to rapid hydrolysis under acidic and basic conditions (at pH values of 5 or below and at pH values of 9 or above) the organomodified trisiloxane surfactants of the present invention provide increased resistance to hydrolysis relative to traditional trisiloxane alkoxylates (Comparative A). An artifact of hydrolysis is observed as a reduction in spreading properties over time. Therefore solutions of the organomodified trisiloxane surfactants of the present invention, as well as comparative surfactants were prepared at desired use levels and pH. Spreading was determined as a function of time to illustrate resistance to hydrolysis.

Table 9 is an illustrative example of the organomodified trisiloxane surfactants, where product No. 3, a superspreader, has improved resistance to hydrolysis, over a pH range from pH 3 to pH 10, relative to a traditional trisiloxane ethoxylate surfactant (Product A). As mentioned above, resistance to hydrolysis was observed by monitoring the spreading properties over time. Here a 0.4 wt % solution was prepared at pH 3, 4, 5 and 10. Spreading determined according to the procedure in Example 4.

TABLE 9

Effect of pH on Spreading Properties Vs Time

| | | Spread Diameter (mm) | | | |
|---|---|---|---|---|---|
| Time | Product | pH 3 | pH 4 | pH 5 | pH 10 |
| 0 h | 3 | 43 | 42 | 43 | 38 |
| | A | 34 | 28 | 29 | 27 |
| 1 h | 3 | 48 | 43 | 46 | 40 |
| | A | 39 | 37 | 27 | 33 |
| 2 h | 3 | 53 | 44 | 50 | 41 |
| | A | 36 | 30 | 33 | 33 |
| 4 h | 3 | 47 | 48 | 52 | 39 |
| | A | 41 | 28 | 28 | 29 |
| 6 h | 3 | 46 | 45 | 48 | 33 |
| | A | 16 | 27 | 27 | 28 |
| 8 h | 3 | 44 | 42 | 47 | 40 |
| | A | 12 | 31 | 29 | 27 |
| 24 h | 3 | 21 | 44 | 46 | 28 |
| | A | 12 | 32 | 25 | 25 |
| 48 h | 3 | 37 | 45 | 43 | 31 |
| | A | 10 | 41 | 25 | 33 |
| 5 days | 3 | 25 | 41 | 40 | 35 |
| | A | 7 | 30 | 26 | 36 |
| 1 wks | 3 | 15 | 37 | 42 | 27 |
| | A | 6 | 17 | 28 | 25 |
| 2 wks | 3 | 11 | 19 | 25 | 27 |
| | A | 7 | 7 | 37 | 15 |

Example 7

The impact of other ingredients on spreading was determined by blending the organosilicone disiloxane surfactant of the present invention, with a conventional organic based co-surfactant. The co-surfactants are described in Table 10.

Blends were prepared as physical mixtures where the weight fraction silicone is represented by a (alpha), indicating that the co-surfactant makes up the balance of the blend ratio. For example when α=0 this indicates that the composition contains 0% of the silicone component and 100% co-surfactant, while an α=1.0 indicates the composition contains 100% silicone, and no (0%) co-surfactant. Mixtures of the two components are represented by the weight fraction α, where a ranges as follows: $0 \leq \alpha \leq 1.0$. By example when α=0.25 this indicates the surfactant mixture is composed of 25% silicone and 75% co-surfactant. These blends are then diluted in water to the desired concentration for spreading evaluation.

Spreading was determined as described in Example 4, at 0.2 wt % total surfactant.

Table 11 demonstrates that representative examples of the co-surfactants of the present invention provide favorable spreading results, and in some cases provide an unexpected synergistic enhancement, where the spread diameter of the mixture exceeds that of the individual components.

TABLE 10

Description of Conventional Co-surfactants

| ID | Description |
|---|---|
| IDA-5 | Isodecyl alcohol ethoxylate (4-5 EO) |
| IDA-6 | Isodecyl alcohol ethoxylate (5-6 EO) |
| TMN-6 | Trimethylnonylalcohol ethoxylate (6 EO) |
| Oxo-TDA-5 | Oxo-tridecyl alcohol ethoxylate (5 EO) |
| Oxo-TDA-6 | Oxo-tridecyl alcohol ethoxylate (6 EO) |
| APG | $C_{8-10}$ Alkylpolyglucoside |

TABLE 11

Effect of Co-surfactants on Blend Spreading Properties

| | | Wt Fraction (α) Silicone Surfactant Spread diameter (mm) | | | | |
|---|---|---|---|---|---|---|
| Run | Silicone | 0 | 0.25 | 0.50 | 0.75 | 1.0 | Co-surfactant |
| 1 | 3 | 47 | 24 | 49 | 52 | 55 | IDA-5 |
| 2 | 3 | 33 | 43 | 51 | 53 | 55 | IDA-6 |
| 3 | 3 | 49 | 48 | 54 | 59 | 55 | TMN-6 |
| 4 | 3 | 47 | 37 | 43 | 47 | 55 | Oxo-TDA-5 |
| 5 | 3 | 43 | 34 | 46 | 48 | 55 | Oxo-TDA-6 |
| 6 | 3 | 8 | 50 | 58 | 49 | 55 | APG |

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

Having described the invention we claim:

1. A silicone composition comprising a silicone having the formula:

$$M^1D^1M^2$$

wherein
   $M^1 = (R^1)(R^2)(R^3)SiO_{1/2}$;
   $M^2 = (R^4)(R^5)(R^6)SiO_{1/2}$; and
   $D^1 = (R^7)(Z)SiO_{2/2}$ where
   $R^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;
   $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group;
   Z is an alkyleneoxide group of the general formula:

$$R^8(C_2H_4O)_a(C_3H_6O)_b(C_4H_8O)_cR^9,$$

where
   $R^8$ is a linear or branched divalent hydrocarbon radical of 3 carbon atoms;
   $R^9$ is selected from the group consisting of H, monovalent hydrocarbon radicals of from 1 to 6 carbon atoms and acetyl, and the subscripts a, b and c are zero or positive and satisfy the following relationships:

$$2a+c, 20 \text{ with a } 2.$$

2. A silicone composition comprising a silicone having the formula:

$$M^1D^1M^2$$

wherein
   $M^1 = (R^1)(R^2)(R^3)SiO_{1/2}$;
   $M^2 = (R^4)(R^5)(R^6)SiO_{1/2}$; and
   $D^1 = (R^7)(Z)SiO_{2/2}$ where
   $R^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;
   $R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group;

Z is an alkyleneoxide group of the general formula:

$$R^8(C_2H_4O)_a(C_3H_6O)_b(C_4H_8O)_cR^9,$$

where
R$^8$ is a linear or branched divalent hydrocarbon radical of 2, 3, 5, 6, 7, 8, or 9 carbon atoms;
R$^9$ is selected from the group consisting of H, monovalent hydrocarbon radicals of from 1 to 6 carbon atoms and acetyl, and the subscripts a, b and c are zero or positive and satisfy the following relationships:

2a+b+c 20 with a 2 where R$^1$ and R$^4$ are selected from the group consisting of propyl, iso-propyl, butyl, sec-butyl, iso-butyl and tert-butyl.

3. The composition of claim 1 where R$^2$, R$^3$, R$^5$, R$^6$ and R$^7$ are methyl.

4. The composition of claim 1 where the subscript a ranges from 8 to 12.

5. The composition of claim 1 where the subscript b ranges from 0 to 3.

6. The composition of claim 1 where the subscript c is 0.

7. The composition of claim 1 where R$^9$ is selected from the group consisting of hydrogen and methyl.

8. The composition of claim 2 where R$^1$ and R$^4$ are selected from the group consisting of iso-propyl and tert-butyl.

9. A silicone composition comprising a silicone having the formula:

$$M^1D^1M^2$$

wherein
$M^1=(R^1)(R^2)(R^3)SiO_{1/2}$;
$M^2=(R^4)(R^5)(R^6)SiO_{1/2}$; and
$D^1=(R^7)(Z)SiO_{2/2}$
where
R$^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;
R$^2$, R$^3$, R$^4$, R$^5$, R$^6$ and R$^7$ are each independently selected from the group consisting of 1 to 4 carbon monovalent hydrocarbon radicals, aryl, and a hydrocarbon group of 4 to 9 carbons containing an aryl group;
Z is an alkyleneoxide group of the general formula:

$$R^8(C_2H_4O)_a(C_3H_6O)_b(C_4H_8O)_cR^9,$$

where
R$^8$ is a linear or branched divalent hydrocarbon radical of 2, 3, 5, 6, 7, 8, or 9 carbon atoms;
R$^9$ is selected from the group consisting of H, monovalent hydrocarbon radicals of from 1 to 6 carbon atoms and acetyl, and the subscripts a, b and c are zero or positive and satisfy the following relationships:

2a+b+c 20 with a 2 where the subscript a is 11.

10. The composition of claim 7 where R$^9$ is hydrogen.

11. The composition of claim 8 where R$^2$, R$^3$, R$^5$, R$^6$ and R$^7$ are methyl.

12. The composition of claim 11 where R$^8$ is a divalent hydrocarbon radical having three carbon atoms.

13. The composition of claim 12 where the subscript a is 11.

14. The composition of claim 13 where the subscripts b and c are both zero.

15. The composition of claim 14 where R$^9$ is hydrogen.

16. A silicone composition comprising a silicone having the formula:

$$M^1D^1M^2$$

wherein
$M^1=(R^1)(R^2)(R^3)SiO_{1/2}$;
$M^2=(R^4)(R^5)(R^6)SiO_{1/2}$; and
$D^1=(R^7)(Z)SiO_{2/2}$
where
R$^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;
R$^2$, R$^3$, R$^4$, R$^5$, R$^6$ and R$^7$ are each independently selected from the group consisting of 1 to 4 carbon monovalent hydrocarbon radicals, aryl, and a hydrocarbon group of 4 to 9 carbons containing an aryl group;
Z is an alkyleneoxide group of the general formula:

$$R^8(C_2H_4O)_a(C_3H_6O)_b(C_4H_8O)_cR^9,$$

where
R$^8$ is a linear or branched divalent hydrocarbon radical of 3 carbon atoms;
R$^9$ is selected from the group consisting of H, monovalent hydrocarbon radicals of from 1 to 6 carbon atoms and acetyl, and the subscripts a, b and c are zero or positive and satisfy the following relationships:

2a+b+c 20 with a 2 wherein said silicone composition has an enhanced resistance to hydrolysis.

17. A silicone composition comprising a silicone having the formula:

$$M^1D^1M^2$$

wherein
$M^1=(R^1)(R^2)(R^3)SiO_{1/2}$;
$M^2=(R^4)(R^5)(R^6)SiO_{1/2}$; and
$D^1=(R^7)(Z)SiO_{2/2}$
where
R$^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;
R$^2$, R$^3$, R$^4$, R$^5$, R$^6$ and R$^7$ are each independently selected from the group consisting of 1 to 4 carbon monovalent hydrocarbon radicals, aryl, and a hydrocarbon group of 4 to 9 carbons containing an aryl group;
Z is an alkyleneoxide group of the general formula:

$$R^8(C_2H_4O)_a(C_3H_6O)_b(C_4H_8O)_cR^9,$$

where
R$^8$ is a linear or branched divalent hydrocarbon radical of 2, 3, 5, 6, 7, 8, or 9 carbon atoms;
R$^9$ is selected from the group consisting of H, monovalent hydrocarbon radicals of from 1 to 6 carbon atoms and acetyl, and the subscripts a, b and c are zero or positive and satisfy the following relationships:

2a+b+c20 with a2 where R$^1$ and R$^4$ are selected from the group consisting of propyl, iso-propyl, butyl, sec-butyl, iso-butyl and tert-butyl.

18. The composition of claim 16 where R$^2$, R$^3$, R$^5$, R$^6$ and R$^7$ are methyl.

19. The composition of claim 16 where the subscript a ranges from 8 to 12.

20. The composition of claim 16 where the subscript b ranges from 0 to 3.

21. The composition of claim 16 where the subscript c is 0.

22. The composition of claim 16 where $R^9$ is selected from the group consisting of hydrogen and methyl.

23. The composition of claim 17 where $R^1$ and $R^4$ are selected from the group consisting of iso-propyl and tert-butyl.

24. A silicone composition comprising a silicone having the formula:

$$M^1D^1M^2$$

wherein
$M^1=(R^1)(R^2)(R^3)SiO_{1/2}$;
$M^2=(R^4)(R^5)(R^6)SiO_{1/2}$; and
$D^1=(R^7)(Z)SiO_{2/2}$ where $R^1$ is selected from the group of monovalent hydrocarbon radicals consisting of branched or linear hydrocarbon group consisting of 2 to 4 carbons, aryl, and an alkyl hydrocarbon group of 4 to 9 carbons containing aryl substituents of 6 to 20 carbon atoms;

$R^2$, $R^3$, $R^4$, $R^5$, $R^6$ and $R^7$ are each independently selected from the group consisting of 1 to 4 carbon monovalent hydrocarbon radicals, aryl, and a hydrocarbon group of 4 to 9 carbons containing an aryl group;

Z is an alkyleneoxide group of the general formula:

$$R^8(C_2H_4O)_a(C_3H_6O)_b(C_4H_8O)_cR^9,$$

where $R^8$ is a linear or branched divalent hydrocarbon radical of 2, 3, 5, 6, 7, 8, or 9 carbon atoms;

$R^9$ is selected from the group consisting of H, monovalent hydrocarbon radicals of from 1 to 6 carbon atoms and acetyl, and the subscripts a, b and c are zero or positive and satisfy the following relationships:

2 a+b+c 20 with a 2.

where the subscript a is 11.

25. The composition of claim 22 where $R^9$ is hydrogen.

26. The composition of claim 23 where $R^2$, $R^3$, $R^5$, $R^6$ and $R^7$ are methyl.

27. The composition of claim 26 where $R^8$ is a divalent hydrocarbon radical having three carbon atoms.

28. The composition of claim 27 where the subscript a is 11.

29. The composition of claim 28 where the subscripts b and c are both zero.

30. The composition of claim 29 where $R^9$ is hydrogen.

31. An aqueous emulsion wherein the discontinuous phase comprises water and the continuous phase comprises the composition of claim 1.

32. An aqueous emulsion wherein the discontinuous phase comprises water and the continuous phase comprises the composition of claim 16.

33. An aqueous emulsion wherein the continuous phase comprises water and the discontinuous phase comprises the composition of claim 1.

34. An aqueous emulsion wherein the continuous phase comprises water and the discontinuous phase comprises the composition of claim 16.

35. A non-aqueous emulsion wherein the discontinuous phase comprises a non-aqueous hydroxylic solvent and the continuous phase comprises the composition of claim 1.

36. A non-aqueous emulsion wherein the discontinuous phase comprises a non-aqueous hydroxylic solvent and the continuous phase comprises the composition of claim 16.

37. A non-aqueous emulsion wherein the continuous phase comprises a non-aqueous hydroxylic solvent and the discontinuous phase comprises the composition of claim 1.

38. A non-aqueous emulsion wherein the continuous phase comprises a non-aqueous hydroxylic solvent and the discontinuous phase comprises the composition of claim 16.

39. A silicone composition comprising a silicone having the formula:

$$M^5D^3M^6$$

wherein
$M^5=(R^{19})(R^{20})(R^{21})SiO_{1/2}$;
$M^6=(R^{22})(R^{23})(R^{24})SiO_{1/2}$; and
$D^3=(R^{25})(Z")SiO_{2/2}$ where $R^{19}$, $R^{20}$, $R^{21}$, $R^{22}$, $R^{23}$, and $R^{24}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms, $R^{25}$ is a linear or branched monovalent hydrocarbon radical of 3 or 4 carbons;

Z" is an alkylene oxide group of the general formula:

$$R^{26}(C_2H_4O)_g(C_3H_6O)_h(C_2H_4O)_iR^{27},$$

where $R^{26}$ is a linear or branched divalent hydrocarbon radical of 2, 3, 5, 6, 7, 8, or 9 carbon atoms;

$R^{27}$ is selected from the group consisting of H, monovalent hydrocarbon radicals of from 1 to 6 carbon atoms and acetyl and the subscripts g, h and i are zero or positive and satisfy the following relationships:

2 g+h+i 20 with g 2.

40. The composition of claim 39 where $R^{27}$ is selected from the group consisting of hydrogen and methyl.

41. The composition of claim 39 where the subscript i is 0.

42. The composition of claim 39 where the subscript h ranges from 0 to 3.

43. The composition of claim 39 where the subscript g ranges from 8 to 11.

44. The composition of claim 39 where $R^{26}$ is a 3 carbon monovalent hydrocarbon radical.

45. The composition of claim 39 where $R^{19}$, $R^{20}$, $R^{21}$, $R^{22}$, $R^{23}$, and $R^{24}$ are methyl.

46. The composition of claim 39 where $R^{25}$ is a 4 carbon monovalent hydrocarbon radical.

47. The composition of claim 46 where $R^{19}$, $R^{20}$, $R^{21}$, $R^{22}$, $R^{23}$, and $R^{24}$ are methyl.

48. The composition of claim 47 where the subscript g is 8.

49. The composition of claim 48 where the subscript h is 0.

50. The composition of claim 49 where the subscript i is 0.

51. A silicone composition comprising a silicone having the formula:

$$M^5D^3M^6$$

wherein
$M^5=(R^{19})(R^{20})(R^{21})SiO_{1/2}$;
$M^6=(R^{22})(R^{23})(R^{24})SiO_{1/2}$; and
$D^3=(R^{25})(Z")SiO_{2/2}$ where $R^{19}$, $R^{20}$, $R^{21}$, $R^{22}$, $R^{23}$, and $R^{24}$ are each independently selected from the group consisting of 1 to 4 carbon monovalent hydrocarbon radicals, aryl, and an alkyl hydrocarbon group of 4 to 9 carbons containing an aryl substituents of 6 to 20 carbon atoms, $R^{25}$ is a linear or branched monovalent hydrocarbon radical of 3 or 4 carbons;

$Z''$ is an alkylene oxide group of the general formula:

$$R^{26}(C_2H_4O)_g(C_3H_6O)_h(C_2H_4O)_iR^{27},$$

where
$R^{26}$ is a linear or branched divalent hydrocarbon radical of 2, 3, 5, 6, 7, 8, or 9 carbon atoms;
$R^{27}$ is selected from the group consisting of H, monovalent hydrocarbon radicals of from 1 to 6 carbon atoms and acetyl and the subscripts g, h and i are zero or positive and satisfy the following relationships:

2 g+h+i 20 with g 2 wherein said silicone composition has an enhanced resistance to hydrolysis.

52. The composition of claim 51 where $R^{27}$ is selected from the group consisting of hydrogen and methyl.

53. The composition of claim 51 where the subscript i is 0.

54. The composition of claim 51 where the subscript h ranges from 0 to 3.

55. The composition of claim 51 where the subscript g ranges from 8 to 11.

56. The composition of claim 51 where $R^{26}$ is a 3 carbon monovalent hydrocarbon radical.

57. The composition of claim 51 where $R^{19}$, $R^{20}$, $R^{21}$, $R^{22}$, $R^{23}$, and $R^{24}$ are methyl.

58. The composition of claim 51 where $R^{25}$ is a 4 carbon monovalent hydrocarbon radical.

59. The composition of claim 58 where $R^{19}$, $R^{20}$, $R^{21}$, $R^{22}$, $R^{23}$, and $R^{24}$ are methyl.

60. The composition of claim 59 where the subscript g is 8.

61. The composition of claim 60 where the subscript h is 0.

62. The composition of claim 61 where the subscript i is 0.

63. An aqueous emulsion wherein the discontinuous phase comprises water and the continuous phase comprises the composition of claim 39.

64. An aqueous emulsion wherein the discontinuous phase comprises water and the continuous phase comprises the composition of claim 51.

65. An aqueous emulsion wherein the continuous phase comprises water and the discontinuous phase comprises the composition of claim 39.

66. An aqueous emulsion wherein the continuous phase comprises water and the discontinuous phase comprises the composition of claim 51.

67. A non-aqueous emulsion wherein the discontinuous phase comprises a non-aqueous hydroxylic solvent and the continuous phase comprises the composition of claim 39.

68. A non-aqueous emulsion wherein the discontinuous phase comprises a non-aqueous hydroxylic solvent and the continuous phase comprises the composition of claim 51.

69. A non-aqueous emulsion wherein the continuous phase comprises a non-aqueous hydroxylic solvent and the discontinuous phase comprises the composition of claim 39.

70. A non-aqueous emulsion wherein the continuous phase comprises a non-aqueous hydroxylic solvent and the discontinuous phase comprises the composition of claim 51.

* * * * *